United States Patent [19]

Spiry

[11] Patent Number: 4,778,386
[45] Date of Patent: Oct. 18, 1988

[54] RING FOR THE CONSTRUCTION OF DENTAL CROWNS AND METHOD OF RESTORATION

[76] Inventor: Jean-Louis Spiry, 76 Rue de Crimée, Paris 75019, France

[21] Appl. No.: 928,249
[22] PCT Filed: Mar. 19, 1986
[86] PCT No.: PCT/FR86/00093
 § 371 Date: Oct. 27, 1986
 § 102(e) Date: Oct. 27, 1986
[87] PCT Pub. No.: WO86/05381
 PCT Pub. Date: Sep. 25, 1986

[30] Foreign Application Priority Data

Mar. 20, 1985 [FR] France ............... 85 04116

[51] Int. Cl.⁴ .................................................. A61C 9/00
[52] U.S. Cl. ........................................... 433/45; 433/40; 433/223
[58] Field of Search ................... 433/183, 283, 34, 40, 433/45, 46, 218

[56] References Cited

U.S. PATENT DOCUMENTS 4,206,545 6/1980 Lord ..................................... 433/183

FOREIGN PATENT DOCUMENTS 2454795 11/1980 France .
2500294 8/1982 France .
2529780 1/1984 France .
2018666 10/1979 United Kingdom .

Primary Examiner—John J. Wilson
Assistant Examiner—Adriene J. Lepiane
Attorney, Agent, or Firm—Young & Thompson

[57] ABSTRACT

Ring for the construction of temporary or permanent dental crowns.

The ring is constituted by two molded half-shells (1, 2) which carry coupling elements (3, 4; 5, 6) rigidly fastened together in pairs by bonding, welding or any other method of rigid attachment which is capable of ensuring cohesion of the assembly in such a manner as to constitute in combination a shuttering mold for the filling product which is intended to restore the tooth.

7 Claims, 3 Drawing Sheets

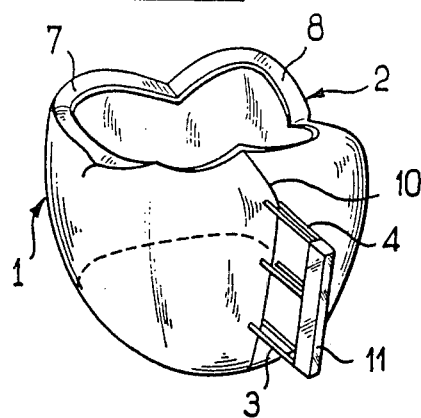
FIG_1
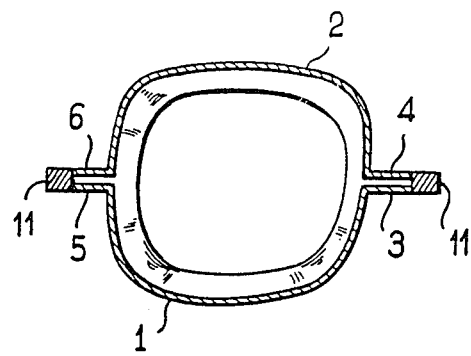
FIG_2
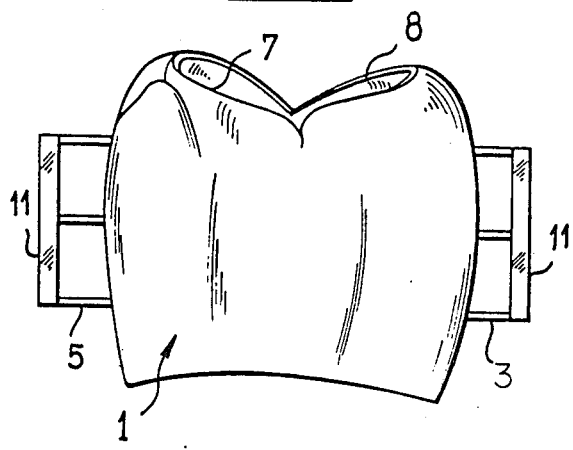
FIG_3
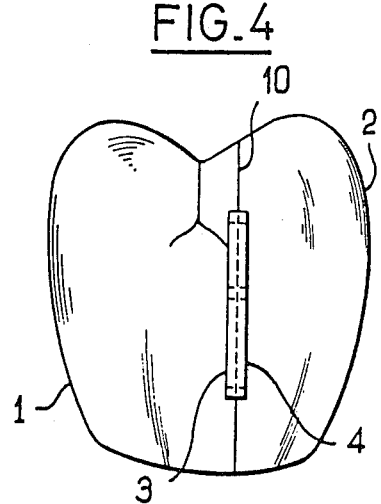
FIG_4
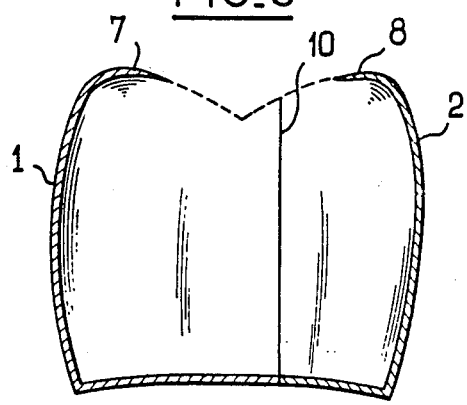
FIG_5
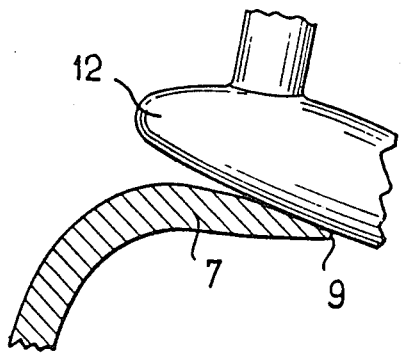
FIG_6

FIG_11
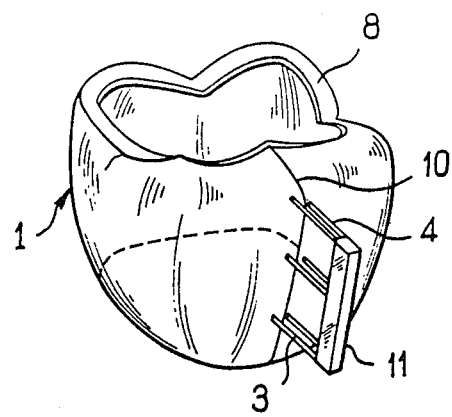
FIG_12
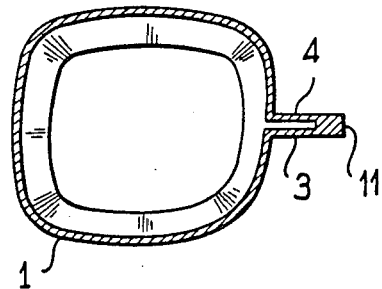
FIG_14
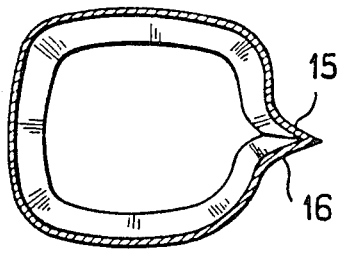
FIG_13
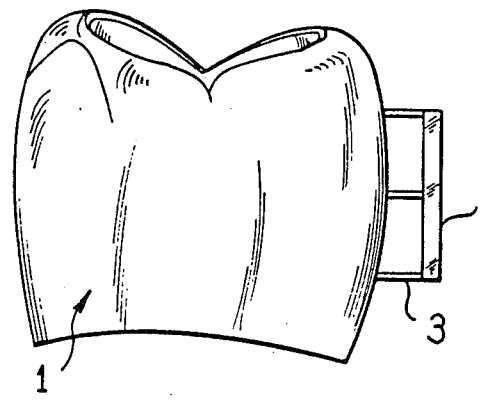
FIG_15
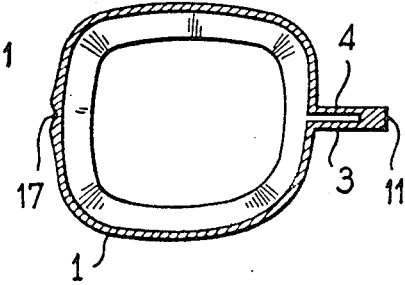

RING FOR THE CONSTRUCTION OF DENTAL CROWNS AND METHOD OF RESTORATION

FIELD OF THE INVENTION

The invention relates to a ring for the construction of dental crowns and to a method of restoration of teeth for the application of said ring. More particularly, the invention relates to a dental ring for use in the manufacture of both temporary and permanent crowns.

BACKGROUND OF THE INVENTION

The temporary crown is a short-term prosthesis which has the intended function of restoring a diseased dental element from the time of preparation of a tooth to the time of sealing of the final prosthesis.

In odontology, the problem of temporary prostheses is one which gives rise to particular concern for at least two reasons. In the first place, it is necessary to meet the classic needs of patients who desire to conceal the unattractive appearance of prepared teeth during the period of construction of prostheses. In the second place, it is necessary to ensure that the temporary prosthesis provides pulp protection of the tooth which has been ground or permits endodontic treatment in the event of substantial decay, restores or maintains a sound periodontium, permits orthodontic displacement if necessary, locks the abutment tooth in its relationships with the opposing and adjacent teeth recorded during the denture impression, and guides the dental prosthetist during preparation of the final prosthesis.

It is already a known practice to construct temporary dental crowns by means of a ring which is placed on and around the previously ground tooth stump to be restored and which is filled with resin. Rings of known types are subject to certain drawbacks. Some rings are of metal, which is aesthetically objectionable, and they are strictly cylindrical, which makes them very unattractive. Preformed rings of polycarbonate are also known. These rings are attended by the following disadvantages: their occlusal faces are stereotyped without any possiblity of adaptation to the opposing teeth. Thus the shape of the temporary crowns obtained from rings of this type does not correspond to the shape of the teeth on which they are positioned. Before fitting them on the teeth, the dentist is consequently obliged to modify their shape in order to adjust them. In the majority of instances, the ring is frusto-conical and flared-out in the downward direction without taking into account the anatomy of a pitted tooth. Furthermore, the open end of the ring must be cut to a festoon shape in order to correspond more or less to the gum contour line.

The final crown is a prosthesis which is sealed or bonded in order to be permanent. The problem of attractive permanent dental crowns is becoming increasingly significant with the appearance of composite resins. In fact, it is possible with these materials to achieve complete restorations of teeth. By making use of amelodentinary adhesives, it is possible to bond these materials to the enamel and to the dentin of teeth.

It is already a known practice to carry out complete tooth restorations by means of a ring which is placed at a tooth location and filled with a composite resin of the type mentioned above. However, these rings are subject to certain disadvantages.

Metallic rings have a frusto-conical shape, which does not usually correspond exactly to the anatomical shape of the other teeth within the oral cavity. This difference in anatomy between a natural tooth and the crown thus formed, which is totally unattractive, may be the cause of poor food deflection which will result in lesions at the level of the marginal gum. Moreover, these metallic rings do not permit the use of photopolymerizable composites. A further point is that no satisfactory method exists for modifying the contour of these rings in order to make them more attractive and to adapt them to the shape of the tooth to be restored and of teeth which are adjacent to this latter.

Rings of celluloid are also known but their extreme deformability is such that they achieve only very imperfect reproduction of the real anatomy. Furthermore, it is difficult to grind them since a grinding operation has the immediate effect of cutting their thin wall.

A matrix for dental use is also known, as disclosed in French patent Application No. 2 454 795, and serves to facilitate the filling of lateral teeth. This matrix consists of a profiled strip having an arcuate transverse cross-section and curved so as to form a closed outwardly bulged ring having dimensions such as to permit approximate restoration of the anatomical shape of a tooth destroyed by dental caries or mechanical influences. This strip is provided with at least one tearing tag which serves to split the matrix into two or more sections so as to facilitate its removal after hardening of the tooth-filling product.

A matrix of this type, however, would not prove suitable for forming a temporary crown which is intended to remain within the oral cavity over a period of several weeks. There are a number of reasons for this: on the one hand, the tearing tags constitute an outward projection and could not be allowed to remain within the patient's mouth. On the second hand, the top edge of the strip forms a sharp projection which, in this case also, cannot be permitted to remain within the mouth. In addition, an effective seal between said edge and any possible filling material could not be maintained for a very long time. Finally, the external profile of the strip is not that of a tooth and is thus also unsuitable for the construction of a crown even of a temporary type.

OBJECTS OF THE INVENTION

One of the objects of the invention is to propose the use of the same ring at the outset for the purpose of forming either a temporary or a permanent dental crown having a particularly attractive appearance, thus overcoming the disadvantages mentioned in the foregoing and making it possible to restore the occlusion as well as the points of contact with the adjacent teeth by means of operations which are particularly simple to perform.

Another object of the invention is to permit construction of said temporary or permanent crown in a single treatment session in the dental surgery without having recourse to the services of a laboratory for the construction of prostheses.

SUMMARY OF THE INVENTION

The invention provides a ring for the construction of either temporary or permanent dental crowns in which a filling product for a tooth to be restored is intended to be received at the location of the tooth to be restored, charcterized in that the ring is obtained by molding and has at least one slit which extends over the full height of the ring, the edges of which have two coupling elements rigidly fastened together and extending over part of the height of the lateral face of the ring, that said ring has a cuspal rim, the shapes of said rim and of the lateral face of the ring being such as to correspond to the external shape of the tooth to be restored, and that the two coupling elements are adapted to permit of separation from the ring after introduction and hardening of the filling product within the ring.

By virtue of its external shape, the ring in accordance with the invention reproduces the external shape of the tooth to be restored, with the result that it can remain in position in the case of a temporary crown. The cuspal rim of said ring not only reproduces the shape of the corresponding edge of a tooth but makes it possible to improve the mechanical bond and fluid-tightness between the ring and the filling product while constituting a mechanical reinforcement of the edge of the temporary crown and thus enabling it to withstand the mechanical stresses produced during the mastication process.

Moreover, taking into account their structure and position, the coupling elements can readily be separated from the ring after hardening of the filling product which has been poured into the ring, thereby ensuring that the patient does not experience any hindrance when the ring is used as a temporary crown.

An important advantage of the present invention lies in the fact that the ring in accordance with the invention can be used without any modification for forming a permanent crown.

In a particular embodiment of the invention, the ring is constituted by two half-shells assembled together by means of two pairs of coupling elements in spaced relation. These two half-shells can readily be molded in the natural and anatomical shape of a tooth and their coupling elements can readily be separated from the ring by sawing and grinding by means of the conventional instruments used by the dentist.

In accordance with further distinctive features of the invention, the coupling elements are rigidly fastened together by bonding, welding, ultrasonic welding or the like;
the ring is translucent;
the external shape of the ring corresponds to the external shape of the tooth to be restored;
the ring is substantially of constant thickness, with the result that the internal shape of the ring corresponds to the external shape of the tooth to be restored;
in the case of a permanent crown, the filling product is a composite resin;
said composite resin is photopolymerizable in order to prevent inclusion of air bubbles within the resin and in order to permit a work period at the dentist's convenience.

The invention also applies a ring of this type to the construction of a temporary crown, characterized in that the ring is retained as an integral part of the temporary crown which can readily remain in place within the patient's mouth over a period of several weeks or more.

Another feature of the invention is the application of a ring of this type to the construction of a permanent crown, characterized in that the ring is used as a shuttering mold for a composite resin and then removed, whereupon the crown is reinforced with resin for constituting the points of contact with the adjacent teeth and compensating for the thickness of the ring which has been removed.

The invention also provides a method for restoring a tooth by means of a temporary crown by making use of a ring in accordance with the invention and a filling product, characterized by the following steps:

the ring with its coupling elements joined together by welding or bonding is placed in position on the tooth to be restored;
the interior of the ring is packed with a filling product;
after hardening of this latter, the ring and the filling product which has been bonded to this latter are removed;
the coupling elements are removed by sawing or cutting; and
the ring is trimmed by grinding opposite to the coupling elements and the temporary crown thus obtained is fitted in position once again within the patient's mouth.

The invention also provides a method for restoring a tooth by means of a permanent crown by making use of a ring in accordance with the invention and a filling product, characterized by the following steps:

the ring with its coupling elements joined together by welding or bonding is placed in position on the tooth to be restored;
the interior of the ring is packed with a filling product which does not adhere to the ring, said filling product being constituted by a composite resin which is photopolymerizable or polymerizable by addition of a polymerizing agent;
the assembly consisting of ring and filling product is removed;
the coupling elements are cut in order to remove the ring;
the crown thus obtained is recharged with filling product in order to compensate for the thickness of the ring and to constitute the points of contact with the adjacent teeth;
the permanent crown thus formed is replaced in position.

BRIEF DESCRIPTION OF THE DRAWINGS

Other distinctive features will become apparent from the following description which is given with reference to the accompanying drawings, in which:

FIG. 1 is a perspective view showing an exemplified embodiment of a ring in accordance with the invention for the construction of temporary or permanent dental crowns, FIG. 2 is a sectional view taken along a horizontal plane of the ring of FIG. 1.

FIG. 3 is a view in a vertical plane at right angles to the axis of alignment of the teeth and showing the ring of FIG. 1, FIG. 4 is an external view in a vertical plane containing the axis of alignment of the teeth and showing the ring of FIG. 1, FIG. 5 is a sectional view taken along the vertical plane containing the axis of alignment of the teeth and showing the ring of FIG. 1, FIG. 6 is an enlarged sectional view of the cuspal rim of the ring of FIG. 5, which serves as a guide for a spatula, FIG. 11 is a view which is similar to FIG. 1 and shows an alternative embodiment of a ring in accordance with the invention for the construction of temporary or permanent dental crowns, FIG. 12 is a sectional view taken along a horizontal plane of the ring of FIG. 11, FIG. 13 is a view taken in a vertical plane at right angles to the axis of alignment of the teeth and showing the ring of FIG. 11, FIGS. 14 and 15 are schematic sectional views relating to alternative embodiments of the ring.

DETAILED DESCRIPTION OF THE INVENTION

Figure 7:
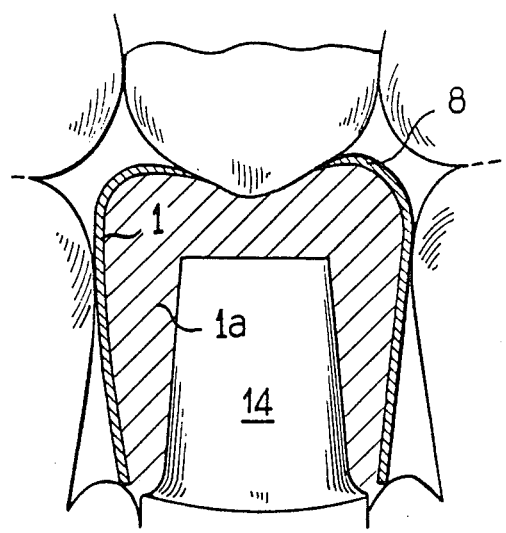
FIG. 7 is a sectional view taken in the vertical plane of alignment of the teeth and showing the position of a crown constructed in accordance with the invention with respect to the adjacent and opposing teeth.

In the embodiment of FIG. 1, it is apparent that the ring in accordance with the invention is composed of two non-identical half-shells 1 and 2 obtained by molding, a cuspal rim 7, 8 being formed at the top of the lateral face of said half-shells so as to leave an opening in the occlusal face of the ring for placement of the filling product inside the ring. It is more readily apparent from FIG. 2 that the two half-shells 1, 2 each carry two coupling elements 3, 5 and 4, 6 respectively which extend over part of the height of the ring. Said coupling elements 3, 5 ; 4, 6 are constituted by strips (see FIG. 3) which have a small cross-section so that they may readily be cut. Said coupling elements 3, 5 ; 4, 6 are placed opposite to each other and are bonded or welded by the ultrasonic technique, for example, on their external edge 11. Welding is performed at a distance from the lateral walls of the ring (see FIGS. 1, 2, 3) in order to ensure that its cross-section at the time of removal from the mold does not modify the crown anatomy. The dividing line between the half-shells 1, 2 is designated by 10 in FIGS. 1, 4 and 5. The plane of the coupling elements 3, 5 ; 4, 6 is preferably located at right angles to the axis of alignment of the teeth with a portion of jawbone. As indicated in FIG. 4, this plane of the coupling elements can be displaced with respect to the plane of symmetry of the tooth in order to avoid interference with the anatomy of the tooth. In accordance with te invention, each half-shell 1 and 2 is of substantially constant thickness, and equal to a few tenths of a millimeter, and is obtained by molding in one piece with its coupling elements 3, 5 ; 4, 6. The exterior of each half-shell has the shape of a tooth, thus ensuring an attractive appearance of the jaw when the ring is employed in a temporary crown. By virtue of the fact that the thickness of the ring is constant, the internal surface is the exact replica of the external surface, thus guaranteeing an attractive appearance of the permanent crown after removal of the ring.

The ring is preferably made of plastic material which permits a certain degree of flexibility such as polycarbonate, for example, and permits coloring right through. It is preferably translucent in order to permit photopolymerization of the filling product when this latter is used for the purpose of making a permanent crown and in order to permit the possibility of controlling the shade of color of the crown.

Different dimensions may be chosen so as to permit the possibility of adapting the rings to all sizes and to the different types of teeth.

In order to use the ring in accordance with the invention as a temporary crown:
  the dental surgeon selects the ring which is best suited to the tooth to be covered;
  the ring then forms a shuttering mold for imparting the requisite shape to the lateral walls of the future crown;
  the ring is then roughly adjusted to the gum. A self-polymerizing resin 1a such as methyl methacrylate or epinine, for example, is deposited inside the ring (see FIG. 7);
  the patient is asked to close his jaws tightly;
  while still in the soft state, the resin 1a is thus compressed on one side by the opposing teeth, on the other side by the gum and the tooth, and laterally by the ring (FIG. 7). This soft resin 1a is thus constrained to mold the top of the crown, the contact points and the limits at the level of the gum.

A chemical bond is established between the ring and the resin 1a. The assembly formed by the ring and the resin is withdrawn from the patient's mouth and ground in order to adjust the cervical edge of the temporary crown at the peripheral limit of the ground tooth 14.

The coupling elements 3, 4 ; 5, 6 are cut or sawn and trimmed by grinding. The temporary crown is then temporarily sealed on the tooth stump 14. The ring is kept as an integral part of the temporary crown.

The temporary crown thus formed is both attractive and durable, with the result that it may remain in position within the patient's mouth over a period of several weeks or months. Mechanical strength of said crown is ensured in particular by the presence of the cuspal rim 7, 8 which constitutes a mechanical reinforcement and at the same time improves the mechanical bond between the filling product 1a and the ring while at the same time forming a tight joint between these latter. Furthermore, said cuspal rim prevents formation of a sharp projection between the filling product and the ring which would be liable to hinder the patient and to reduce the useful life of the crown.

Figure 8:
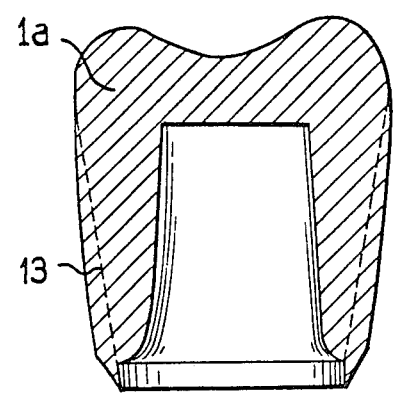
FIG. 8 is a view showing the crown obtained after removal of the ring and showing in dashed lines the excess portion of filling product to be removed in the case of a permanent or temporary crown.

In order to use the ring in accordance with the invention as a permanent crown, the ring is chosen so as to circumscribe the prepared tooth 14 completely. It is roughly adjusted with respect to the gum and maintained between its collateral teeth by means of wedges of wood or of plastic material. A composite resin 1a is placed within the ring or preferably injected into this latter and then photopolymerized if this option is adopted. The occlusal face is formed by the patient who is asked to apply pressure by biting (FIG. 7) and the opposing teeth thus mold the filling resin 1a. It is possible to improve the impression of the occlusal face by applying pressure on the cuspal rim 7 with a spatula 12 (see FIG. 6) and following its contour 9. When polymerization of the material within the ring is completed, the assembly consisting of ring and composite resin 1a is withdrawn from the patient's mouth. In this case, the composite resin 1a does not adhere to the ring. The welded joints 11 formed between the coupling elements of the two half-shells 1, 2 are cut with a view to removing the mold from the final crown of composite resin (see FIG. 8). The dashed line 13 delimits the excess portion of resin to be removed by grinding.

Figure 9:
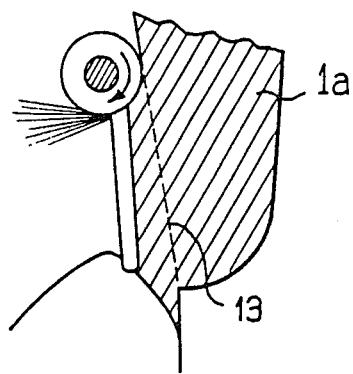
FIG. 9 is an enlarged fragmentary sectional view of the crown to a larger scale showing the grinding operation for removal of the excess portion.
Figure 10:
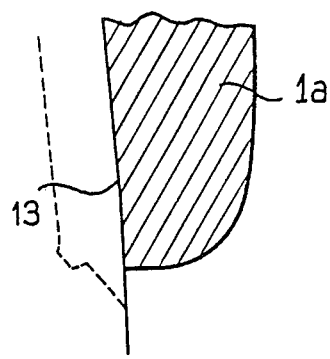
FIG. 10 is a view which is similar to FIG. 9 and shows the crown obtained on completion of the grinding operation.

The restorative crown thus obtained is adjusted at the level of the gum by grinding (see FIGS. 9 and 10) in order to remove the excess portion down to the surface 13. This grinding operation is facilitated by the fact that the cervical limit of the preparation is impressed in the restoration.

The points of contact of the crown with the adjacent teeth are reinforced with composite resin 1a in order to compensate for the thickness of the ring. Finally, the crown is either bonded or sealed to the ground tooth stump 14.

In the simplified embodiment shown in FIGS. 11, 12, 13, the ring obtained by molding is provided in the same manner as in the preceding embodiment with a single slit 10 which extends over the full height of the ring and the edges of which have two coupling elements 3, 4 rigidly fastened together by bonding or welding and extending over part of the height of the lateral wall of the ring. Said ring also has a cuspal rim 8, the shape of said rim and the shape of the lateral face of the ring being such as to correspond to the external shape of the tooth to be restored. As in the preceding embodiment, the two coupling elements 3, 4 are so arranged that they can be separated from the ring by sawing or cutting after introduction and hardening of the filling product 1a within the ring.

The method of construction of a temporary or permanent crown by means of the ring shown in FIGS. 11 to 13 is similar to the method described earlier with reference to FIGS. 7 to 10.

The ring in accordance with the invention offers many advantages. In the first place, it has the same external shape as a natural tooth. Its structural design in the form of two half-shells or in the form of a split ring permits fabrication of the ring by molding in two parts or in a single part of constant thickness, thus ensuring that the filling resin has the external shape of a natural tooth. The shade of color of the ring can correspond to that of a tooth. It can be translucent in order to permit the use of photopolymerizable resins. It permits positioning of a temporary or permanent crown in a single treatment session. Finally, the ring ensures the construction of dental crowns which have a particularly attractive appearance without any need to take impressions or to resort to the services of a laboratory for the manufacture of prostheses.

As will readily be apparent, the invention is not limited to the examples described in the foregoing and any number of modifications of these latter can be made without thereby departing from the scope of the present invention.

Thus, as indicated in FIG. 14, the two adjacent coupling elements 15, 16 can be molded in one piece with the remainder of the ring. Moreover, the V-shape of these two coupling elements 15, 16 endows the ring with a degree of elasticity which makes it possible to fit this latter in position on teeth which have slightly different diameters.

In the case of FIG. 15, provision is made for a zone 17 of reduced thickness on the side opposite to the coupling elements 4, 3, thus providing the ring with an outward appearance which closely resembles the anatomy of a natural tooth and thus constituting an articulation which facilitates de-molding of the ring.

Moreover, the coupling elements 4, 3 could be joined to the ring, not by means of small-section strips, but by means of zones of reduced thickness constituting a line of incipient rupture of said coupling elements.

We claim:
1. Ring for the construction of either temporary or permanent dental crowns in which a filling product for restoring a tooth to be restored, said ring being the location of the tooth to be restored, said ring being obtained by molding and having at least one slit (10) which extends over the full height of the ring and the edges of which have two coupling elements (3, 4) projecting from the lateral face of the ring and rigidly fastened together a substantial distance from said lateral face, said ring having a cuspal rim (8), the shapes of said rim and of the lateral face of the ring being such as to correspond to the external shape of the tooth to be restored, and the two coupling elements (3, 4) being adapted to be sawed to permit separation from the ring of the portions of the coupling elements that are rigidly fastened together after introduction and hardening of the filling product (1a) within the ring.

2. Ring according to claim 1, constituted by two half-shells (1, 2) assembled together by means of two pairs of coupling elements (3, 4; 5, 6) in spaced relation, these two half-shells being each provided with a cuspal rim (7, 8).

3. Ring according to claim 1, wherein the ring is substantially of constant thickness so that the internal shape of the ring corresponds to the external shape of the tooth to be restored.

4. Ring according to claim 1, wherein the external edges (11) of the coupling elements (3, 4; 5, 6) are rigidly fastened together by bonding, welding, ultrasonic welding or the like.

5. Ring according to claim 1, wherein the coupling elements (3, 4; 5, 6) are constituted by smallsection strips.

6. Method for restoring a tooth by means of a temporary crown by making use of a ring obtained by molding and having at least one slit (10) which extends over the full height of the ring and the edges of which have two coupling elements (3, 4) rigidly fastened together and projecting from the lateral face of the ring, said ring having a cuspal rim (8) the shapes of said rim and of the lateral face of the ring being such as to correspond to the external shape of the tooth to be restored, comprising the following steps:
the ring is placed within the patient's mouth at the location of the tooth to be restored;
the interior of the ring is packed with a filling product (1a) which adheres to the ring;
after hardening of said filling product, the ring and the filling product which has been bonded to this latter are removed;
the coupling elements (3, 4; 5, 6) of said ring are removed by sawing or cutting;
the ring is trimmed by grinding opposite to the coupling elements, and
the temporary crown thus obtained is refitted within the patient's mouth.

7. Method for restoring a tooth by means of a permanent crown by making use of a ring obtained by molding and having at least one slit (10) which extends over the full height of the ring and the edges of which have two coupling elements (3, 4) rigidly fastened together and projecting from the lateral face of the ring, said ring having a cuspal rim (8) the shapes of said rim and of the lateral face of the ring being such as to correspond to the external shape of the tooth to be restored, comprising the following steps:

the ring is placed in position within the patient's mouth at the location of the tooth to be restored;

the interior of the ring is packed with a filling product (1a) consisting of a composite resin which does not adhere to the ring, which is photopolymerizable or polymerizable by addition of a polymerizing agent;

the assembly consisting of ring and filling product (1a) is removed;

the coupling elements (3, 4; 5, 6) are cut in order to remove the ring;

the crown thus obtained is recharged with filling product (1a) in order to compensate for the thickness of the ring and to constitute the points of contact with the adjacent teeth;

the permanent crown thus formed is refitted in position.

* * * * *